United States Patent
Kobayashi et al.

(10) Patent No.: US 11,602,561 B2
(45) Date of Patent: Mar. 14, 2023

(54) TREATMENT METHOD AND SYSTEM FOR EPIDEMIC KERATOCONJUNCTIVITIS

(71) Applicant: CSP Advanced Solutions Inc., Abiko (JP)

(72) Inventors: Masahiko Kobayashi, Aichi (JP); Masayuki Takasu, Abiko (JP); Akira Mizuno, Nagoya (JP)

(73) Assignee: CSP ADVANCED SOLUTIONS INC., Abiko (JP)

( * ) Notice: Subject to any disclaimer, the term of this patent is extended or adjusted under 35 U.S.C. 154(b) by 852 days.

(21) Appl. No.: 16/448,650

(22) Filed: Jun. 21, 2019

(65) Prior Publication Data

US 2020/0000913 A1 Jan. 2, 2020

Related U.S. Application Data

(60) Provisional application No. 62/691,144, filed on Jun. 28, 2018.

(51) Int. Cl.
*A61K 41/00* (2020.01)
*A61K 41/10* (2020.01)
(Continued)

(52) U.S. Cl.
CPC ............ *A61K 41/10* (2020.01); *A61F 9/0008* (2013.01); *A61F 9/0026* (2013.01); *A61K 9/08* (2013.01);
(Continued)

(58) Field of Classification Search
CPC .......... A61K 41/10; A61K 9/08; A61K 41/00; A61K 47/02; A61K 47/36; A61P 27/02;
(Continued)

(56) References Cited

U.S. PATENT DOCUMENTS

| 2015/0340207 A1* | 11/2015 | Holbeche .......... H01J 37/32532 118/723 R |
| 2016/0264274 A1* | 9/2016 | Kulaga .................... B65B 55/12 |
| 2017/0094769 A1* | 3/2017 | Eckert .................. A61B 18/042 |

FOREIGN PATENT DOCUMENTS

| JP | 201698196 A | 5/2016 |
| WO | 2009041049 A1 | 1/2011 |
| WO | PCTJP2019024648 | 9/2019 |

OTHER PUBLICATIONS

Mizuno, A., et al., "Inactivation mechanism of Bacteriophages subjected to atmospheric pressure nonequilibrium plasma," 27th Annual Meeting of the Japan Society of Plasma Science and Nuclear Fusion Research, Gakujyutu Koryu Kaikan, Hokkaido University Sapporo campus, Dec. 1, 2010, 1 page. (with English translation).

(Continued)

*Primary Examiner* — Xiuyu Tai
(74) *Attorney, Agent, or Firm* — Perilla Knox & Hildebrandt LLP; Kenneth A. Knox

(57) ABSTRACT

A plasma activated ophthalmic solution generating device operable to generate a therapeutic ophthalmic solution for curing epidemic keratoconjunctivitis includes a plasma generating electrode operable to generate a plasma activated ophthalmic solution for epidemic keratoconjunctivitis, wherein the plasma generating electrode is arranged surrounding an insert space where a unit dose ophthalmic eyedrop container with a container body, which seals a certain solution in a sterile state, is inserted; a power supply unit; and a high voltage generating unit, which is connected to the power supply unit, operable to be supplied with power source from the power supply unit and to apply high voltage electric current to the plasma generating electrode. This configuration makes it possible to provide a novel and effective therapeutic ophthalmic solution for epidemic keratoconjunctivitis (EKC).

19 Claims, 10 Drawing Sheets

(51) Int. Cl.
    *A61F 9/00*     (2006.01)
    *H05H 1/24*     (2006.01)
    *A61K 47/02*     (2006.01)
    *A61K 9/08*     (2006.01)
    *A61P 27/02*     (2006.01)
    *A61K 47/36*     (2006.01)
    *H05H 1/48*     (2006.01)
    *H05B 41/24*     (2006.01)

(52) U.S. Cl.
    CPC .............. *A61K 41/00* (2013.01); *A61K 47/02* (2013.01); *A61K 47/36* (2013.01); *A61P 27/02* (2018.01); *H05B 41/24* (2013.01); *H05H 1/24* (2013.01); *H05H 1/2406* (2013.01); *H05H 1/48* (2013.01); *H05H 1/481* (2021.05)

(58) Field of Classification Search
    CPC ........ H05H 1/481; H05H 1/24; H05H 1/2406; H05H 1/48; A61F 9/0008; A61F 9/0026; H05B 41/24
    See application file for complete search history.

(56) References Cited

OTHER PUBLICATIONS

Murray, B., et al., "Virion disruption by ozone-mediated reactive oxygen species," Journal of Virological Methods, vol. 153, Issue 1, Oct. 2008, pp. 74-77.

Zimmermann, J.L., et al., "Effects of cold atmospheric plasmas on adenoviruses in solution," Journal of Physics D: Applied Physics, vol. 44, Nov. 30, 2011, 505201, pp. 1-9.

Sakudo, A., et al., "Nitrogen Gas Plasma Generated by a Static Induction Thyristor as a Pulsed Power Supply Inactivates Adenovirus," PLOS ONE, Jun. 20, 2016, pp. 1-17.

Mizuno, A., et al., "Destruction of biological particles using nonthermal plasma," J. Clin. Biochem. Nutr., vol. 60, No. 1, Jan. 2017, pp. 12-24.

Yasuda, H., et al., "Biological Evaluation of DNA Damage in Bacteriophages Inactivated by Atmospheric Pressure Cold Plasma," Plasma Processes and Polymers, 2010, vol. 7, pp. 301-308.

Kobashiri, R., et al., "Investigation of chemical species in plasma treated water essential for inactivation of cells and proteins," Lecture collections 2016 by the Institute of Electrostatics Japan, 2016, pp. 215-216. Abstract.

Alekseev, O., et al., "Nonthermal Dielectric Barrier Discharge (DBD) Plasma Suppresses Herpes Simplex Virus Type 1 (HSV-1) Replication in Corneal Epithelium," Translational Vision Science & Technology, vol. 3, No. 2, Mar. 1, 2014, pp. 1-14.

Rosani, U., et al., "Atmospheric-Pressure Cold Plasma Induces Transcriptional Changes in Ex Vivo Human Corneas," PLOS ONE, vol. 10, No. 7, Jul. 23, 2015, pp. 1-17.

Thirumdas, R., et al., "Plasma activated water (PAW): Chemistry, physico-chemical properties, applications in food and agriculture," Trends in Food Science and Technology, vol. 77, May 4, 2018, pp. 21-31.

Kobayashi, M., et al., European Search Report, EP Application No. 19825775.0, Feb. 10, 2022, 9 pages.

Yasuda, H., et al., "Biological Evaluation of DNA Damage in Bacteriophages Inactivated by Atmospheric Pressure Cold Plasma," Plasma Process. Polym., 2010, 7, pp. 301-308.

\* cited by examiner

FIG. 2a
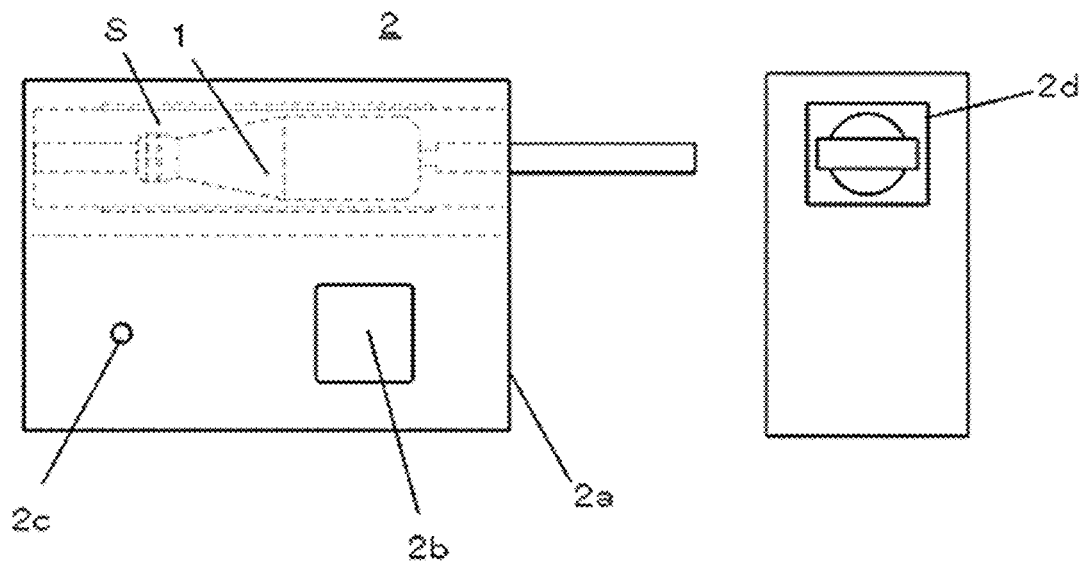
FIG. 2b
FIG. 2c
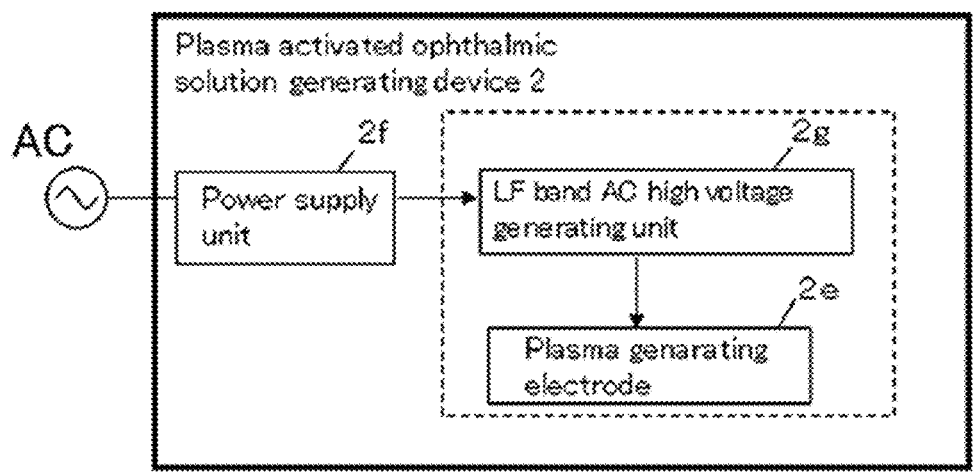

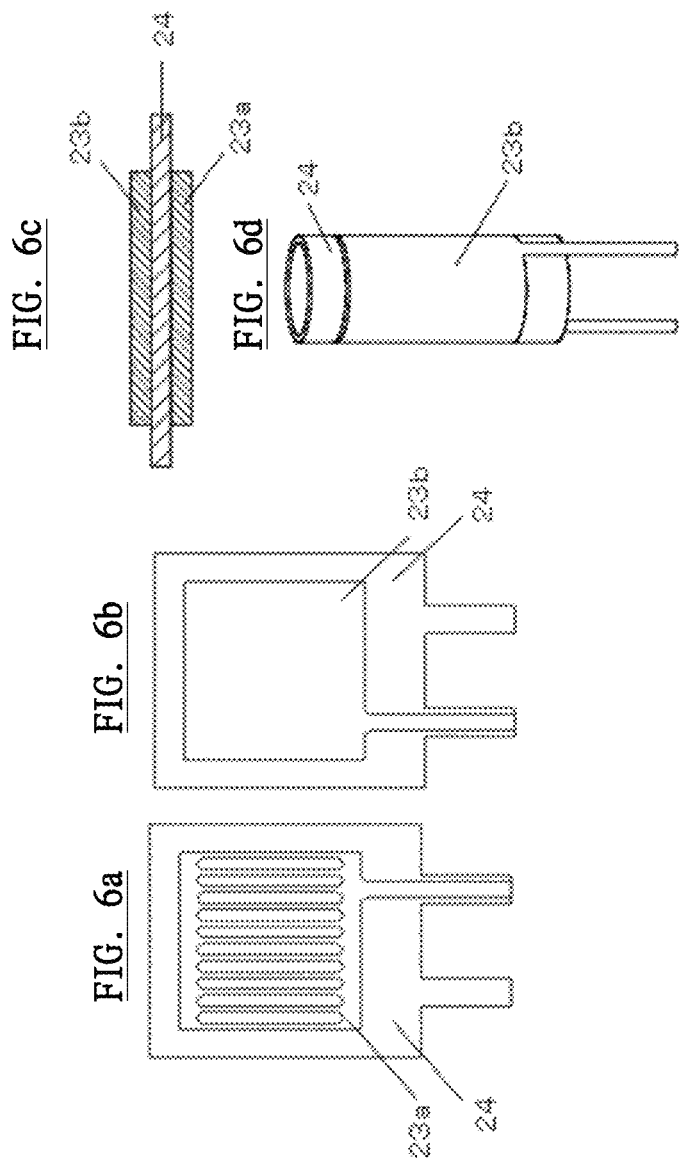

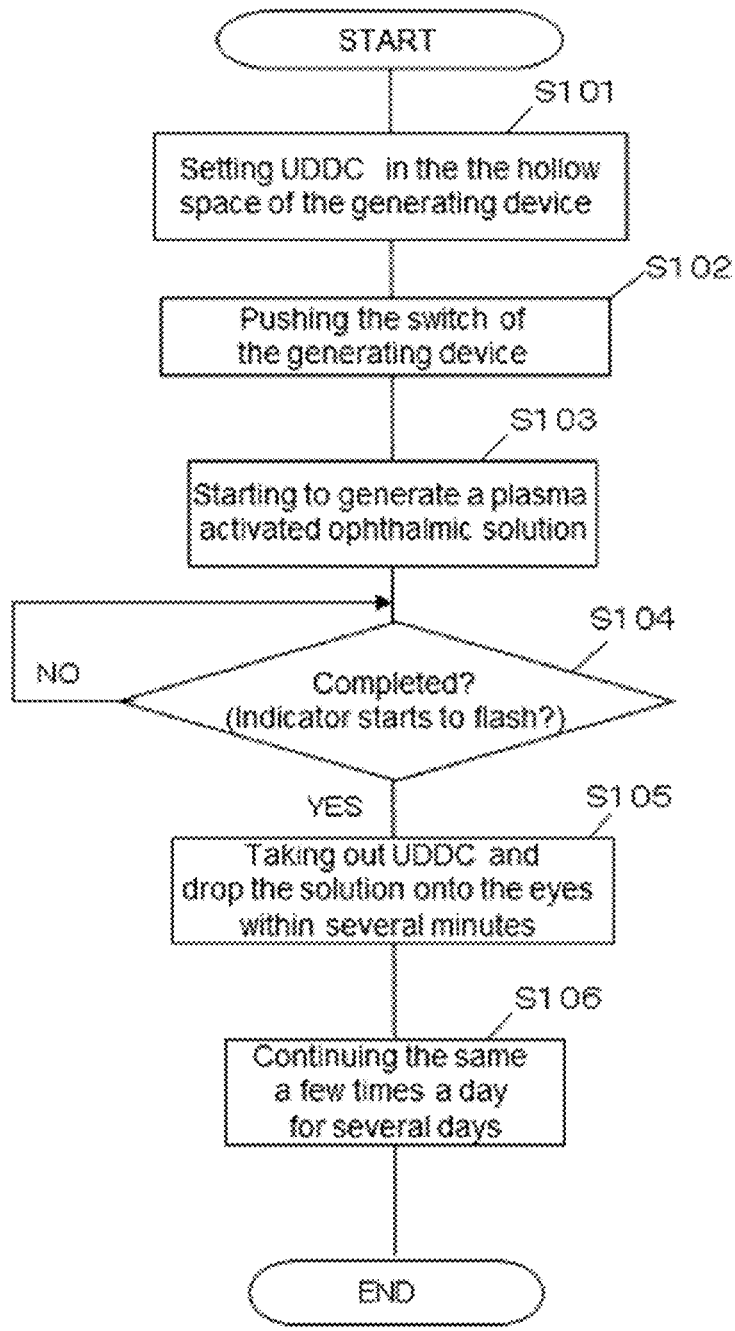

TREATMENT METHOD AND SYSTEM FOR EPIDEMIC KERATOCONJUNCTIVITIS

CROSS-REFERENCE TO RELATED APPLICATIONS

This application claims the benefit of U.S. Provisional Application No. 62/691,144, filed on Jun. 28, 2018, the complete disclosure of which, in its entirety, is hereby incorporated by reference.

BACKGROUND OF THE INVENTION

1. Field of the Invention

The present invention relates to a therapeutic ophthalmic solution for epidemic keratoconjunctivitis (EKC), a plasma activated ophthalmic solution generating device for generating the solution, and a therapeutic method for epidemic keratoconjunctivitis.

2. Description of the Related Art

Conjunctivitis is known as a disease to cause inflammation of conjunctiva, which is the outermost layer of the white part of the eye and the inner surface of the eyelid. There are several types of conjunctivitis such as, bacterial conjunctivitis caused by an infection, viral conjunctivitis and allergic conjunctivitis caused by an allergy.

Epidemic keratoconjunctivitis, which is sometimes called EKC, is a disease caused mainly by Species D and E Adenovirus and infectious mainly by contact through hands and splash such as sneezing. EKC is categorized as an epidemic infectious disease. People are usually infected at the places where many people gather like workplaces and homes. Medical institutions also become the epicenter of the disease as personnel experience close contact with infected patients.

In general, the incubation period of EKC is 8 to 14 days. After the period, symptoms such as swelling of the eyelids, itching and lacrimation develop suddenly. Adenovirus is highly contagious and could easily infect both eyes, but symptoms of the first infected eye are stronger. When inflammation spreads to the cornea, the transparency of the cornea is damaged and its opacity might last for several years. Sometimes conjunctivitis becomes hemorrhagic and may require diagnose whether it is hemorrhagic conjunctivitis or pharyngeal conjunctival fever. Hundreds of thousands of people in Japan and 20 million people throughout the world, including not serious cases, get conjunctivitis each year.

Conventionally, the way to kill or sterilize bacteria and viruses is classified in a physical technique using heat or pressure and a chemical technique using medicine. However, a plasma sterilization technology, which is safer and can sterilize bacteria and viruses instantly, has recently been spreading gradually.

A plasma technology has recently been applied to many fields such as electric, chemical, material and medical field. Not only charged particles such as electron and ion, but also ultraviolet rays and radical are generated in a plasma condition. It is becoming clear that these things can sterilize tissues and have various benefits to some tissues. For example, a method and an apparatus for pasteurization is disclosed in WO2009/041049, the complete disclosure of which, in its entirety, is hereby incorporated by reference. For this method, in order to destroy bacteria present in a liquid or on the surface of a liquid, plasma is irradiated onto the liquid under the pH condition of the liquid adjusted to 4.8 or below. Generated super oxide anion radicals and hydroperoxy radicals might have the effect of sterilization in this reference. In addition, a plasma sterilization technology is also disclosed in H. Yasuda, T. Miura, H. Kurita, K. Takashima, A. Mizuno, Plasma Process. Polym. 2010, 7, 301-308, the complete disclosure of which, in its entirety, is hereby incorporated by reference.

Particularly, non-equilibrium discharge plasma (low-temperature plasma) under a released atmospheric state is versatile because it can produce a lot of radicals under an atmospheric state. Due to the low temperature of the gas, non-equilibrium discharge plasma can prevent sterilized objects from being damaged by heat. It is also inexpensive because the device of non-equilibrium plasma discharge is simple and does not require a ventilation device. With this non-equilibrium discharge plasma, the plasma process can be carried out around a room temperature, and it can kill microorganisms and inactivates viruses. It is predicted that virus epidemics caused by new influenza, foot-and-mouth disease and so on will become a serious problem in the future. Therefore, a plasma sterilization technology using non-equilibrium low-temperature plasma that does not require using medicine and inducing chemical resistance, is expected a lot to be helpful in order to inactivate a virus.

BRIEF SUMMARY OF THE INVENTION

Under the circumstances, at present, there is no effective drug against viral infectious disease such as EKC caused by Adenovirusesm. The current treatment for EKC is by applying eye drops containing an anti-inflammatory agent symptomatically. In case where inflammation or turbidity is found in cornea, a steroid drug is used as a therapeutic agent. If there is a possibility of mixed infection of bacteria, eye drops containing antibacterial agents are to be applied to the eyes.

The present invention has been made in view of the above-mentioned problems, and has an object to provide a novel and effective therapeutic ophthalmic solution for epidemic keratoconjunctivitis, a plasma activated ophthalmic solution generating device for generating the solution, and a therapeutic method for epidemic keratoconjunctivitis.

DISCLOSURE OF INVENTION

In order to solve the abovementioned issues, the present invention is a plasma activated ophthalmic solution generating device operable to generate a therapeutic ophthalmic solution for curing epidemic keratoconjunctivitis, the device comprising; a power supply unit; a plasma generating electrode that is arranged surrounding an insert space, in which a unit dose ophthalmic eyedrop container with a container body is inserted, wherein the container body seals a certain solution in a sterile state; and a high voltage generating unit, which is connected to the power supply unit, operable to be supplied with power source from the power supply unit and to apply high voltage electric current to the plasma generating electrode, wherein the plasma generating electrode generates a plasma activated ophthalmic solution for curing epidemic keratoconjunctivitis by receiving high voltage electric current from the high voltage generating unit.

In this generating device, preferably, wherein the high voltage generating unit is a low frequency (LF) band AC high voltage generating unit, and wherein the plasma generating electrode irradiates non-thermal equilibrium plasma onto the unit dose ophthalmic solution container at atmospheric pressure by receiving high voltage electric current from the low frequency (LF) band AC high voltage generating unit.

In this generating device, preferably, wherein the certain solution in the unit dose ophthalmic eyedrop container is a plasma irradiating solution, wherein approximately half a volume of the container body is filled with gas and air, and wherein the high voltage generating unit applies AC voltage comprising approximately 2-10 kV as a drive voltage, approximately 0.1-0.5 A as a drive current, and approximately 30-80 KHz as a frequency, to the plasma generating electrode in order to generate the plasma activated ophthalmic solution.

In this generating device, preferably, wherein the plasma irradiating solution comprises super-pure water, sodium hyaluronate solution or silver nitrate solution, or a mixed solution comprising any of the super-pure water, sodium hyaluronate solution or silver nitrate solution.

In this generating device, preferably, wherein the plasma generation electrode comprises an electrode wire as a core and a dielectric coating the surface of the electrode wire, wherein the plasma generating electrode is formed spirally, and wherein the unit dose ophthalmic eyedrop container is mounted into a hollow space of the plasma generation electrode.

In this generating device, preferably, wherein the plasma generating electrode comprises a dielectric, which is a thin film, the inner surface and the outer surface of the dielectric are coated with a film-like electrode, the plasma generating electrode is rounded approximately cylindrically, and the unit dose ophthalmic eyedrop container is inserted into a hollow space of the plasma generating electrode.

In this generating device, preferably, wherein a material of the electrode wire comprises any of flexible copper wire, stainless wire, aluminum wire, iron wire or gold wire, or alloy wire comprising any of flexible copper wire, stainless wire, aluminum wire, iron wire or gold wire, wherein a material of the dielectric is a polymer with a siloxane bond or a polymer having imide bonds of a plurality of aromatic compounds.

In this generating device, preferably, wherein a material of the electrode wire comprises any of flexible copper wire, stainless wire, aluminum wire, iron wire or gold wire, or alloy wire comprising any of flexible copper wire, stainless wire, aluminum wire, iron wire or gold wire, wherein a material of the dielectric is a polymer with a siloxane bond or a polymer having imide bonds of a plurality of aromatic compounds.

In this generating device, preferably, further comprising an insulated housing part, wherein the housing part comprising: an insertion hole in which the unit dose ophthalmic eyedrop container is inserted; a switch part that initiates plasma irradiation; and an indicator that indicates a completion of plasma irradiation to a user.

In order to solve the abovementioned issues, the present invention is a unit dose ophthalmic eyedrop container operable to be inserted in the plasma activated ophthalmic solution generating, comprising a container body operable to seal a certain solution that is irradiated by plasma in a sterile state, and a bottle cap connected to the container body.

In this container, preferably, wherein the certain solution in the unit dose ophthalmic eyedrop container is a plasma irradiating solution, wherein approximately half a volume of the container body is filled with gas and air, and wherein the unit dose ophthalmic eyedrop container is made up with low density polyethylene.

In this container, preferably, wherein the plasma irradiating solution comprises super-pure water, sodium hyaluronate solution or silver nitrate solution, or a mixed solution comprising any of the super-pure water, sodium hyaluronate solution or silver nitrate solution.

In order to solve the abovementioned issues, the present invention is a therapeutic ophthalmic solution for epidemic keratoconjunctivitis, wherein the therapeutic ophthalmic solution is generated by irradiating non-thermal equilibrium plasma onto a plasma irradiating solution at atmospheric pressure with the usage of the plasma activated ophthalmic solution generating device.

In this solution, preferably, wherein the plasma irradiating solution comprises super-pure water, sodium hyaluronate solution or silver nitrate solution, or a mixed solution comprising any of the super-pure water, sodium hyaluronate solution or silver nitrate solution.

In order to solve the abovementioned issues, the present invention is a plasma activated ophthalmic solution generating method for epidemic keratoconjunctivitis, comprising; (a) a high voltage generating step of being supplied with power source and applying high voltage electric current to a plasma generating electrode; and (b) a plasma activated ophthalmic solution generating step of generating a plasma activated ophthalmic solution for curing epidemic keratoconjunctivitis by irradiating plasma onto a certain solution inside a unit dose ophthalmic eyedrop container having a container body, in which the certain solution is sealed in a sterile state.

In order to solve the abovementioned issues, the present invention is a therapeutic method for epidemic keratoconjunctivitis, comprising; (a) a setting step of setting the unit dose ophthalmic eyedrop container of the generating device in a hollow space of the plasma activated ophthalmic solution generating device of the generating device before an eyedrop instillation; (b) a initiating step of initiating a switch of the plasma activated ophthalmic solution generating device as a trigger for starting plasma irradiation to the container; (c) a taking out step of taking out the container from the plasma activated ophthalmic solution generating device after completing plasma irradiation; and (d) an eye-dropping step of dropping the solution onto an eye of a user within a predetermined period after removing a cap of the container.

In this method, preferably, wherein the predetermined period is within 10 minutes from a completion of the plasma irradiation.

In order to solve the abovementioned issues, the present invention is an eye-drop kit for curing epidemic keratoconjunctivitis, comprising a package consisting of the plasma activated ophthalmic solution generating device and the unit dose ophthalmic eyedrop container.

BRIEF DESCRIPTION OF THE DRAWINGS

The present invention will be described hereinafter with reference to the annexed drawing. It is to be noted that the drawing is shown for the purpose of illustrating the technical concepts of the present invention or embodiments thereof, wherein:

FIG. 2a shows a front view as one example of the plasma activated ophthalmic solution generating device.

FIG. 2b shows a right side view as one example of the plasma activated ophthalmic solution generating device.

FIG. 2c shows a function block diagram as one example of the plasma activated ophthalmic solution generating device.

FIG. 6a shows an explanatory drawing of a structure (inner surface) of a plasma generating electrode according to a second example.

FIG. 6b shows an explanatory drawing of a structure (outer surface) of the plasma generating electrode according to the second example.

FIG. 6c shows a sectional view of the plasma generating electrode according to the second example.

FIG. 6d shows a perspective view of the plasma generating electrode according to the second example.

FIG. 7 is a flowchart showing the processes of a therapeutic method for epidemic keratoconjunctivitis using the generating device.

DETAILED DESCRIPTION OF THE INVENTION

Embodiments of the present invention will be described hereinafter with reference to the drawings. It is to be understood that the embodiments described herein are not intended as limiting, or encompassing the entire scope of the present invention.

EMBODIMENTS

Referring from FIG. 1a to FIG. 8, a novel and effective therapeutic ophthalmic solution for epidemic keratoconjunctivitis, a plasma activated ophthalmic solution generating device for generating the solution, and a therapeutic method for epidemic keratoconjunctivitis will be explained.

First, Adenovirus, which causes epidemic keratoconjunctivitis (EKC), will be described. Adenovirus is a virus having a small spherical shape. Adenovirus has 70~90 mm in diameter, DNA and a capsid structure (an icosahedron). There are 12 projections with an antenna shape on the surface of Adenovirus cell. Adenovirus does not have an envelope comprising protein and lipid.

Adenovirus can produce symptoms such as conjunctivitis, sore throat, high fever and the like. Adenovirus is a comparatively common virus. At present, 51 kinds of serum types are registered in terms with Adenovirus. Among these types, serum types causing conjunctivitis are known as Ad3, 4, 7, 8, 11, 19, 37, 54, 56 type. These serum types have excellent affinity with the surface cell of the conjunctiva and an infection starts in a state when the fiber of Adenovirus connects to the receptor of the host cell. Then, an encapsulant is formed in the nucleus of the cell and the infected cell will be destroyed. The destruction speed depends on the type of the serum.

The inventors of the present invention paid attention to a plasma phenomenon, which can inactivate viruses such as Adenovirus causing EKC. The inventors have found necessary medical ways that can inactivate Adenovirus, which exist on the surface of a cornea and a conjunctiva, by applying a special solution, on which a plasma is irradiated under a certain condition, onto the surface of the cornea.

Next, referring to FIG. 1, the configurations of a Unit Dose ophthalmic Dropper Container (UDDC) used for EKC treatment will be explained. FIG. 1 shows a schematic figure of UDDC 1. UDDC 1 comprises a container body 1a and a bottle cap 1b connected to the container body 1a. The container body 1a has approximately 50 mm width×10 mm depth×10 mm height. The container body 1a can be inserted into a plasma activated ophthalmic solution generating device mentioned below and has enough size to be mounted therein.

Figure 1A:
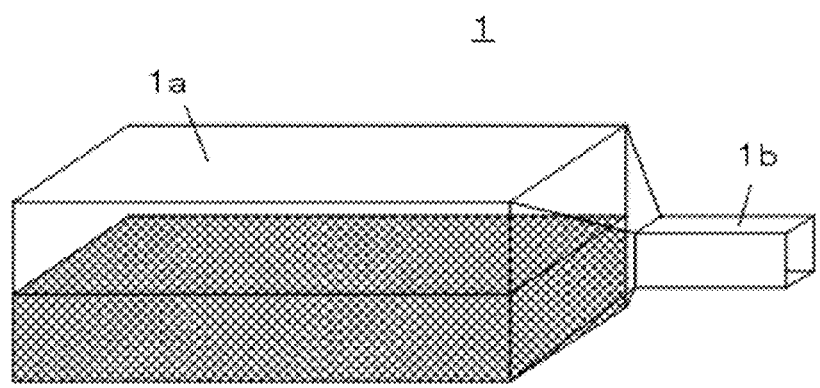
FIG. 1a shows an explanatory drawing of a Unit Dose ophthalmic Dropper Container (UDDC), which is inserted in a plasma activated ophthalmic solution generating device.
Figure 1B:
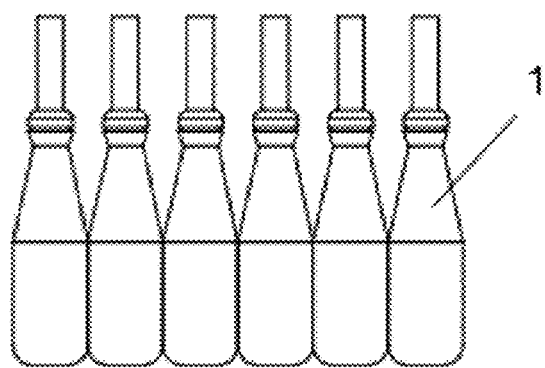
FIG. 1b shows an image drawing of the UDDC.

A plasma irradiating solution (for example approx. 0.5 ml), which is irradiated by plasma, is sealed in the container body 1a in a sterile state, and approximately half the volume of the container body 1a is filled with gas and air. The plasma irradiating solution comprises super-pure water, sodium hyaluronate solution or silver nitrate solution, or a mixed solution comprising any of the super-pure water, sodium hyaluronate solution or silver nitrate solution. It is needless to say that other solution, which can be inactivated by plasma, is also applicable. UDDC 1 is made up with low density polyethylene (LDPE) or a similar resin thereof. UDDC 1 can be sold as a part of an eyedrop kit for treating EKC. For example, UDDC 1 can be sold in the form of a package as shown in FIG. 1b.

Next, referring to FIG. 2, a plasma activated ophthalmic solution generating device (hereinafter referred to as "generating device") used for EKC treatment will be described. The generating device 2 irradiates plasma to UDDC 1 and can activate the plasma irradiating solution inside the container body 1a and a plasma activated ophthalmic solution for curing EKC is generated in the end. The generating device 2 is very small, light and handy. The generating device 2 has approximately 50 mm width×20 mm depth× 100 mm height and its weight is about 10 g.

The generating device 2 comprises a housing part 2a that is insulated due to conduct a plasma irradiation to UDDC 1. The housing part 2a comprises a switch part 2 that initiates plasma irradiation, an indicator 2c that indicates plasma irradiation conditions such as a completion of plasma irradiation to a user, and an insertion hole 2d in which UDDC 1 can be inserted.

The configurations of the generating device 2 will be explained. As shown in FIG. 2c, the generating device 2 comprises a plasma generating electrode 2e, a power supply unit 2f connected to AC power source, and a low frequency (LF) band AC high voltage generating unit (high voltage generating unit) 2g. The plasma generating electrode 2e is arranged surrounding an insert space S where UDDC 1 having the container body 1a, which can seal a certain solution in a sterile state, is inserted therein. The plasma generating electrode 2e irradiates plasma to the solution inside UDDC 1 and generates a plasma activated ophthalmic solution for treating EKC. The power supply unit 2f is arranged in the housing part 2a and is connected to a battery or a commercial power supply and the like. The generating device 2 can be driven by a small battery or a commercial power supply. The LF band AC high voltage generating unit 2g is connected to the power supply unit 2f and is supplied with power source therefrom and applies high voltage electric current to the plasma generating electrode 2e. Herein, the low frequency band AC high voltage generating unit 2g applies an electric field to the plasma generating electrode 2e intermittently. In this state, electrons only receive an energy so that the temperature of the electrons becomes higher than the temperature of gas temperature. This condition is called a non-equilibrium discharge plasma (low-temperature plasma) under a released atmospheric state.

The plasma generating electrode 2e is characterized in comprising metal and dielectric, and is connected to the LF band AC high voltage generating unit 2g, and generates plasma between electrodes by receiving high voltage current. Herein, UDDC 1 is arranged between electrodes of the plasma generating electrode 2e. The plasma generating electrode 2e has the best plasma generation method and conditions in order to generate a plasma activated ophthalmic solution which can inactivate Adenovirus.

Figure 3:
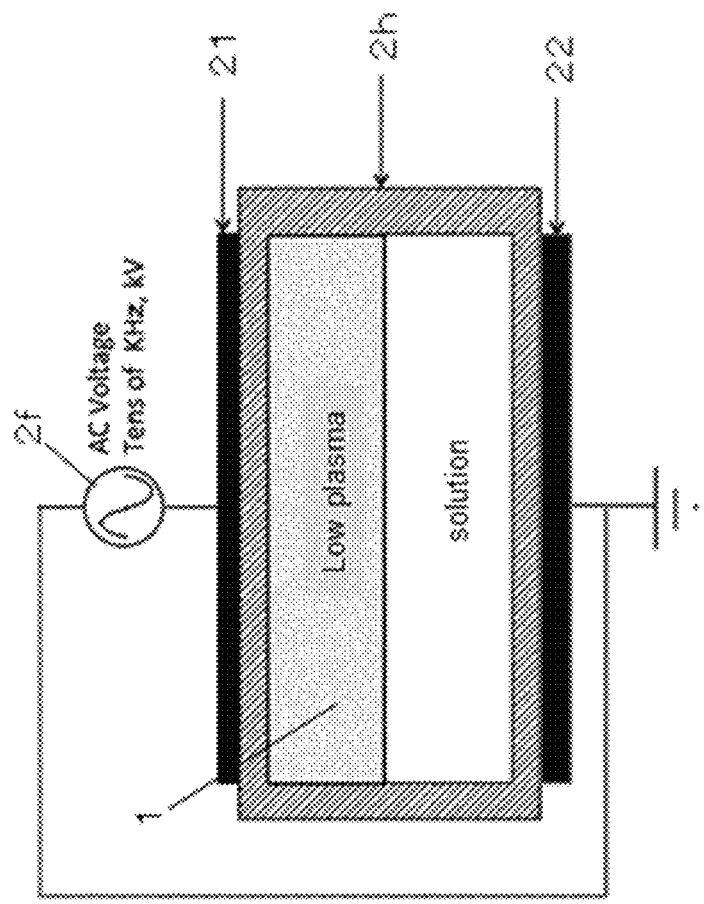
FIG. 3 shows a diagram as one example of the Plasma generation circuit, which is equipped with the plasma activated ophthalmic solution generating device.

Next, referring to FIG. 3, a plasma generation circuit, which is equipped with the generating device 2, will be explained. FIG. 3 shows a conceptual diagram of the plasma generation circuit. Basically, it requires the power supply unit 2f and the plasma generating electrode 2e.

In this embodiment, the plasma generation circuit comprises a pair of the plasma generating electrodes 2e and the power supply unit 2f, which applies an AC voltage to the pair of the plasma generating electrodes 2e. As described below, the pair of the plasma generating electrodes 2e forms dielectric film such as polysiloxane on the surface thereof. Plasma condition is generated in a discharge space when an AC voltage from the power supply unit 2f is applied to the pair of the plasma generating electrodes 2e.

More specifically, the plasma generating electrode 2e shown in FIG. 3 has electrodes 21,22 using parallel flat electrodes. In this embodiment, AC 4 kV p-p with the frequency of around 40 kHz is applied between the electrodes 21,22. UDDC 1 is placed between the high voltage electrode 21 and the grounding electrode 22. Herein, there is an insulating barrier 2h, which is about 2 mm gap, between UDDC 1 and the high voltage electrode 21 or the grounding electrode 22. This insulating barrier 2h is equivalent to a plasma irradiation distance. This plasma irradiation distance will also become an important factor when it comes to generating a plasma activated ophthalmic solution with the most sufficient sterilization effectiveness. Therefore, the distance between UDDC 1 and the high voltage electrode 21 or the distance between UDDC 1 and the grounding electrode 22 can be shorter as much as they can.

Furthermore, it is possible for gas to be sealed in this insulating barrier 2h. For example, the kind of the gas is air, helium, argon, nitrogen, mixed gas thereof and a mixed gas with oxygen and nitrogen diluted with argon or helium. A Low-temperature plasma is created between the electrodes 21,22 via the insulating barrier 2h and radicals generated in it are injected in the solution in UDDC 1 and then a plasma activated ophthalmic solution is generated in the end. The kinds of the generated radicals, which are an oxygen radical, hydroxyl radicals, an ozone radical and the like, depend on the kind of the gas.

Figure 8:
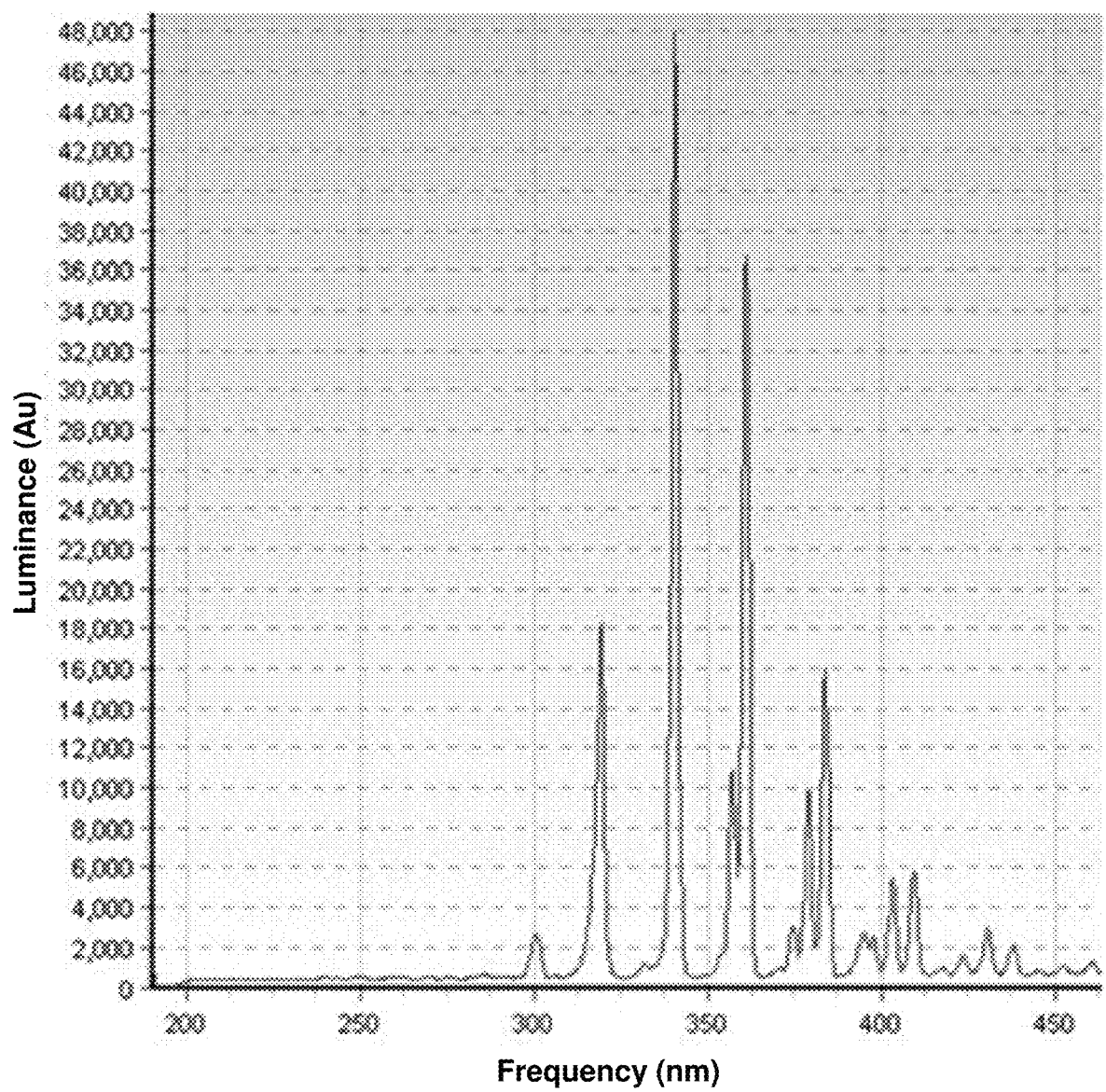
FIG. 8 shows a spectral waveform caused from the plasma generating electrode of the generating device.

A plasma activated ophthalmic solution (PAOS) is a solution generated by the generating device 2. The generating device 2 can irradiate plasma to UDDC 1, which is sealed a sterilized ophthalmic solution. Under a plasma condition, electron, ion, radical, light, electric field and so on are generated. In addition, oxygen radical, nitrogen radical, hydroxyl radicals, nitrogen monoxide and so on are generated by reacting plasma with oxygen, nitrogen and vapor. In this embodiment, hydrogen peroxide, nitrate ion, nitrite ion and the like are generated in the plasma activated ophthalmic solution. In addition, reaction products by reacting with the contents of the solution are also generated, these generated products can oxidize and decompose the capsid of Adenovirus. A virus DNA inside the capsid is attacked by oxygen radical, ultraviolet and the like so that Adenovirus becomes inactivated in the end. In order to determine the inactivation of Adenovirus, the inventors examined how viruses are damaged by the plasma irradiation via a dielectric barrier discharge system with the use of A phage, which is a kind of *Escherichia coli*. The result is shown in FIG. 8 mentioned below.

First Example

Next, the first example of the plasma generating electrode 2e equipped with the generating device 2 will be described with reference to FIG. 4. In this first example, the plasma generating electrode 2e, which can generate plasma, is a type of dielectric barrier discharge, which can be possible to miniaturize the generating device 2.

Conventionally, there are many types of devices that is capable of generating plasma. Dielectric barrier discharge is known as one type and can generate plasma by forming dielectric on the surface of electrodes. Dielectric is made of glass, ceramic and the like. Nitrogen molecules existing in the air are very stable and applying extreme high voltage is required to shift from nitrogen molecules to plasma condition with ionized molecules. In terms with a conventional way using ceramic, it is not capable of downsizing a device due to restriction of flexibility of electrodes shape, and shape stability after being generated by high temperature burning is very low, and the production cost is very high, and decreasing its weight is very difficult. Dielectric barrier discharge using ceramic still has many problems such with using high voltage, which is lead to large power consumptions.

On the other hand, the plasma generating electrode 2e according to this first example can solve above-mentioned conventional issues. The plasma generating electrode 2e is very flexible of its shape, cheap and low power consumptions so that the plasma generating device having excellent mass productivity and better flexibility can be provided with the plasma generating electrode 2e.

Figure 4A:
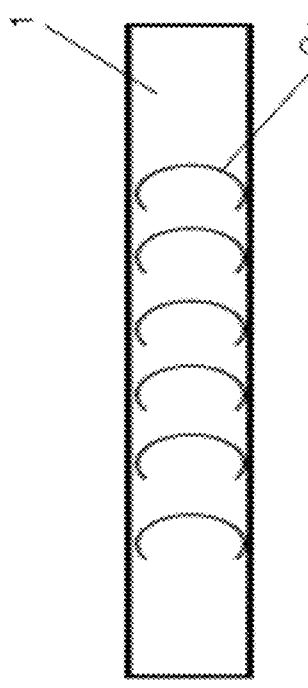
FIG. 4a shows an explanatory drawing of a structure of a plasma generating electrode according to a first example.
Figure 4B:
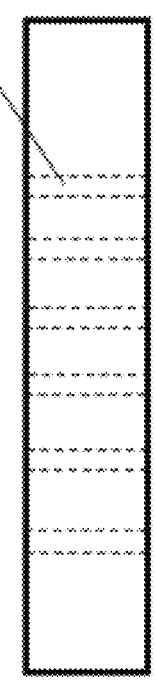
FIG. 4b shows an explanatory drawing of said structure according to the first example.
Figure 4C:
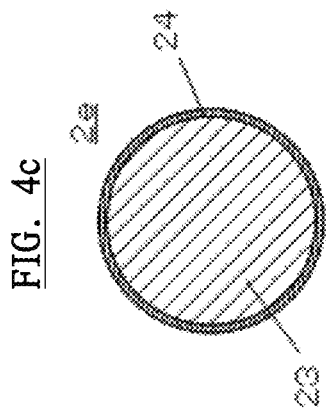
FIG. 4c shows a sectional view of the plasma generating electrode according to the first example.

Specifically, referring to FIGS. 4a-4c, an electrode structure of the plasma generating electrode 2e according to this first example will be explained. FIG. 4a and FIG. 4b are conceptual diagrams of the plasma generating electrode 2e from front side. For example, the plasma generating electrode 2e is liner, and its cross-sectional shape is round. A pair of electrodes 2e is fabricated into a twisted structure. As shown in FIG. 4c, the plasma generating electrode 2e comprises an electrode wire 23 as a core and a dielectric 24 coating the surface of the electrode wire 23. As shown in FIG. 4a and FIG. 4b, the plasma generating electrode 2e is formed spirally. UDDC 1 is mounted into a hollow space thereof. Therefore, the space between UDDC 1 and the plasma generating electrode 2e can be tighter as much as they can. Herein, the structure of the plasma generating electrode 2e is not limited thereto. Plate structure, pipe structure and the like are also applicable. The electrodes 24 can have a film structure.

As shown in FIG. 4c, the electrode wire 23 is coating with the dielectric 24. In this case, the section diameter of the electrode wire 23 is about 5 mm while the film thickness of the electrodes 24 is about 50-200 μm. The thicker the dielectric 24 is, the stronger the electrode wire 23 becomes. However, if the dielectric 24 is thicker, it is difficult to cause an electric discharge. As a result, it requires higher voltage. Therefore, it is preferable to make the thickness of the dielectric 24 thinner within an allowable range of a resistance.

The material of the electrode wire 23 comprises any of flexible copper wire, stainless wire (SUS wire), aluminum wire, iron wire or gold wire, or alloy wire comprising any of flexible copper wire, stainless wire, aluminum wire, iron wire or gold wire. The electrode wire 23 does not always be spiral, in some cases, it is formed as ring-shaped. The shape of the electrode wire 23 is not limited to the shape shown in FIGS. 4a-4c, it can be formed as a pair of plate electrodes coated with a dielectric.

Figure 5A:
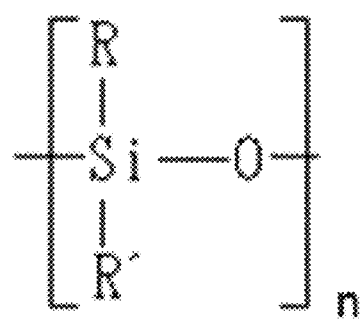
FIG. 5a shows a chemical structure of polycyclohexane coated on the surface of the plasma generating electrode according to the first example.
Figure 5B:
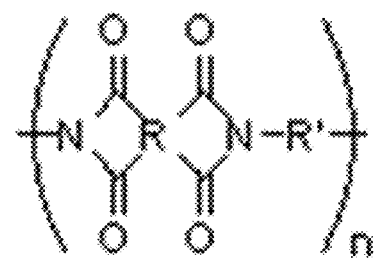
FIG. 5b shows a chemical structure of Polyimide coated on the surface of the plasma generating electrode according to the first example.

The material of the dielectric 24 is a polymer (polysiloxane) with a siloxane bond where silicon and oxygen are connected in a liner manner as shown in FIG. 5a, or a polymer (polyimide) having imide bonds of a plurality of aromatic compounds as shown in FIG. 5b. Herein, a dielectric strength is in proportion with the gap between an electrode and a dielectric. dielectric strength is inversely in proportion with the thickness of the dielectric. Therefore, the gap should be minimized, and the thickness of the dielectric should be minimized so that plasma can be generated with low voltage and high efficiency.

The form such as oiling state (silicon oil), rubber state (silicon rubber), resin state (silicon-base resin, silicon resin) varies by changing R,R' or polymerization degree n. Herein, R,R' can be $CH_3$ or $C_6H_5$. FIG. 5b shows a formula including polyimide. In case where R and R' are aromatic compounds, it is called an aromatic polyimide. Most polyimides for industrial purposes use this aromatic polyimide. The dielectric 24 uses these polymers as the material. The electrode wire 23 is coated with the material and the material is dried so that the dielectric 24 having a certain thickness is formed on the surface of the electrode wire 23. As a result of this, in the first example, the electrode wire 23 has a flexibility of the shape. Herein, the generating way of the dielectric 24 is not limited in the above-mentioned way. For example, dipping, brush coating, spraying or screen printing is also applicable.

Furthermore, conventionally, a atmospheric pressure plasma generating device uses solid materials such as ceramic and glass for a dielectric material. This makes it difficult to miniaturize the device, provide a flexible device and reduce the weight of the device. In addition, this requires higher voltage in order to generate a discharge. On the other hand, in terms with the plasma generating electrode 2e according to the first example, the dielectric 24 can be formed with the process of coating and drying and the thickness of the dielectric 24 can be about 100 μm. This makes it much more efficient to shorten the discharge distance regardless of the electrode shape. As a result of this, the energy required for a discharge can be minimized and it can generate plasma with an electrical power consumption of several watts. Since it can enhance a flexibility of the shape of the dielectric 24, it can generate plasma with very simple electrode structure. And it is possible to change the shape of twisted wires.

Next, the electrical characteristics of the generating device 2 according to the first example will be described. When operating, the LF band AC high voltage generating unit 2g applies AC voltage, which comprises approximately 2-10 kV as a drive voltage, approximately 0.1-0.5 A as a drive current, and approximately 30-80 KHz as a frequency, to the plasma generating electrode.

Second Example

Herein, as the second example, the plasma generating electrode 2e has a electrode structure as shown in FIGS. 6a-6d. In the second example, the plasma generating electrode 2e comprises the dielectric 24, which is a thin film. The inner surface and the outer surface are coated with film-like electrode 23a, 23b, and the plasma generating electrode 2e is rounded approximately cylindrically as shown in FIG. 6d. UDDC 1 is inserted into a hollow space thereof.

Next, referring to the flowchart shown in FIG. 7, a therapeutic method for epidemic keratoconjunctivitis using the generating device according to the embodiment will be described.

First, a user such as a EKC patient sets UDDC 1 in the hollow space of the generating device 2 before instillation (S101). Then, the user pushes the switch 2b as a trigger for starting plasma irradiation (S102). Then, the generating device 2 starts to irradiate plasma onto UDDC 1 sealing a sterilized ophthalmic solution and can generate a plasma activated ophthalmic solution in UDDC 1 (S103). And then, after completing the generation of the plasma activated ophthalmic solution (Yes in S104), the indicator 2c of the generating device 2 indicates the completion to the user by lighting up or flashes.

And then, the user takes out UDDC 1 from the generating device 2, and the user is required to remove the cap 1b of UDDC1 and drop the solution onto the eyes within a predetermined period (for example, the predetermined period is within 10 minutes from a completion of the plasma irradiation) (S105). This is because the conditions of radicals and ions in the plasma activated ophthalmic solution vary depending to the period after the completion, the inventors have found that the most effective and stable way to cure EKC is to instill the solution onto the eyes right after the completion. Finally, the user keeps this treatment a few times a day, every few hours and for several days in order to perfectly cure a contagious viral disease such as EKC (S106).

As described above, the plasma activated ophthalmic solution generating device 2 operable to generate a therapeutic ophthalmic solution for curing epidemic keratoconjunctivitis, the device 2 comprising; a power supply unit 2f; a plasma generating electrode 2e that is arranged surrounding an insert space, in which a unit dose ophthalmic eyedrop container 1 with a container body 1a is inserted, wherein the container body 1a seals a certain solution in a sterile state; and a high voltage generating unit 2g, which is connected to the power supply unit 2f, operable to be supplied with power source from the power supply unit 2f and to apply high voltage electric current to the plasma generating electrode 2e, wherein the plasma generating electrode 2e generates a plasma activated ophthalmic solution for curing epidemic keratoconjunctivitis by receiving high voltage electric current from the high voltage generating unit 2g.

This configuration makes it possible to provide a novel and effective therapeutic ophthalmic solution for epidemic keratoconjunctivitis (EKC) and the plasma activated ophthalmic solution generating device 2 for generating the ophthalmic solution. In other words, the generating device 2 irradiates plasma to the plasma irradiating solution in the UDDC 1 (or a solution in the generating device 2) under certain conditions in order to generate the plasma activated solution. And then, the plasma activated solution is instilled to viruses and Adenovirus within the predetermined conditions so that sterilization and inactivating viruses can be achieved.

Furthermore, the inventors have succeeded in obtaining a virus inactivating effect, especially for Adenovirus, by dropping the plasma activated ophthalmic solution on the surface of an organism (cell) in order to exclude the risk such as a corneal problem by irradiating plasma onto the surface of the eyes directly. In particular, active oxygen species generated by irradiating non-thermal equilibrium plasma at atmospheric pressure or a pressure near atmospheric pressure promote inactivation of viruses (infection ability) by oxidizing and decomposing the capsid of viruses. Plasma (radical) with a preferable density, which does not affect normal cells, can destroy the capsid only and can exhibit an excellent anti-viral activity.

Herein, there are a variety of supply forms of this invention. An eye-drop kit for curing EKC comprising a package, which consists of the generating device 2 and UDDC 1, can be provided to the users.

Experimental Results

Next, the irradiation level of the plasma generating electrode 2e being equipped with the generating device 2 according to this embodiment will be examined. FIG. 8 shows the emission spectrum under conditions where the generating device 2 generates plasma in the atmosphere. Ultraviolet emission, $N_2$ plasma emission, and $O_2$ plasma emission with strong luminance between the range 10-400 nm of frequency were observed. Based on this result, it is thought that radicals caused by these Ultraviolet emission, $N_2$ plasma emission, and $O_2$ plasma emission in the plasma activated ophthalmic solution can exterminate Adenovirus.

Figure 9:
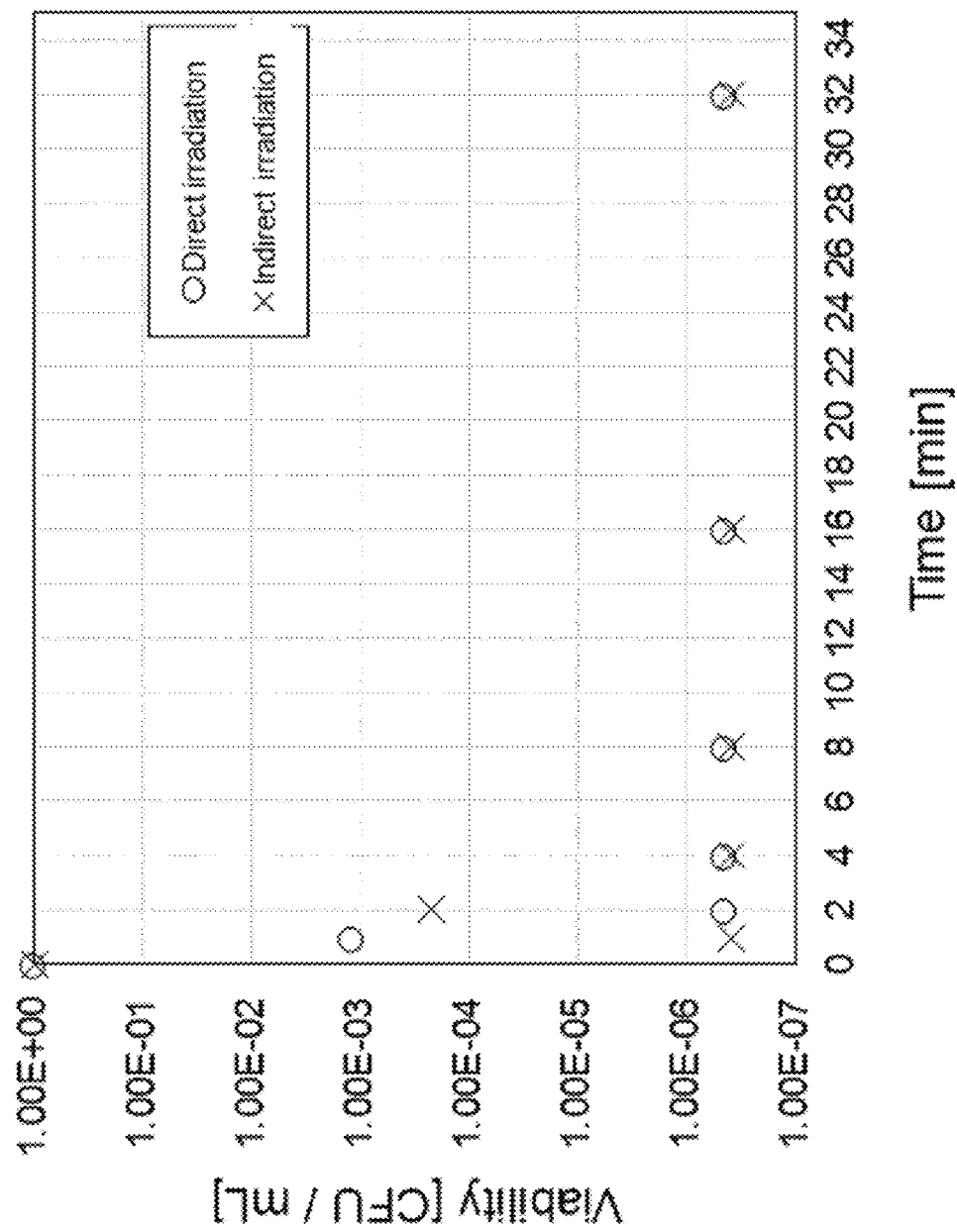
FIG. 9 shows experimental results demonstrating sterilizing ability of the plasma activated ophthalmic solution.
Figure 10:
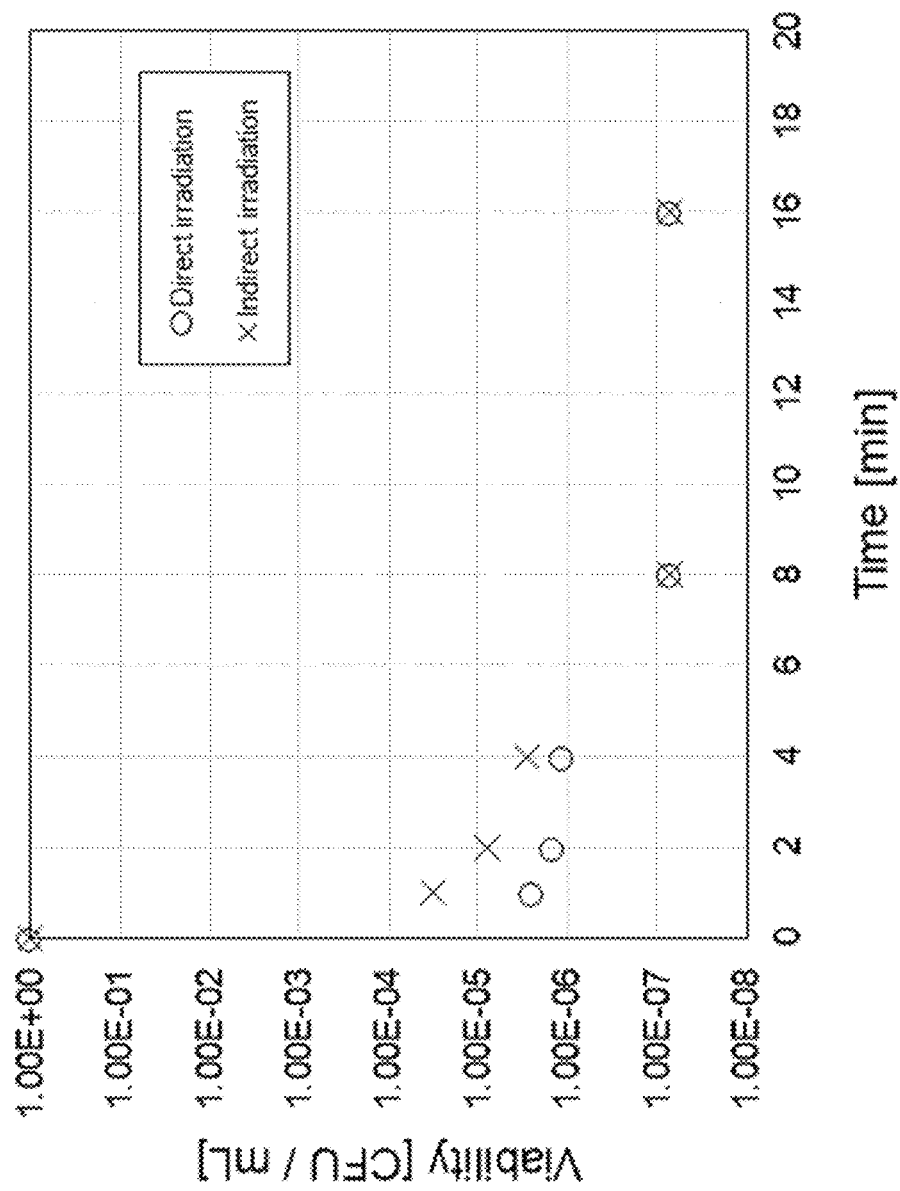
FIG. 10 shows experimental results demonstrating sterilizing ability of the plasma activated ophthalmic solution.

FIG. 9 and FIG. 10 show experimental results demonstrating sterilizing ability of the plasma activated ophthalmic solution according to this embodiment. Herein, *E. coli* ATCC13706 and φX174 phage (a virus infected by a bacteria) were used as a test sample. Herein, CFU in this figure stands for Colony Forming Unit and is a unit for the amount of bacteria. For example, 20 CFU/ml means 20 bacteria in 1 ml. Because *E. coli* ATCC13706 and φX174 phage are exterminated after plasma irradiation, the vertical axis shows the relative values (viability) of survived number of bacteria at each time, provided that the number of bacteria before the irradiation sets as 1 (1.00E+00).

Experiment 1

The purpose of this Experiment 1 is to clarify the effect of direct irradiation. In terms with the conditions, MilliQ water and suspension 0.5 mL having *E. coli* ATCC13706 1.E+08 were poured into a laboratory dish, and the concentration of this sample solution was adjusted to $2\times10^8$/mL, and the electrodes of the discharge device is put 2 mm distance from the suspension. The number of the bacteria was measured 0, 1, 2, 4, 8, 16, 32 minutes after the irradiation. The result is shown (○) in FIG. 9.

Next, under the same conditions using φX174 phage instead of *E. coli*, the result is shown (○) in FIG. 10.

As shown in FIG. 9 and FIG. 10, rapid sterilizing ability was observed in this direct irradiation. This shows that the capsids and cellular walls of *E. coli* ATCC13706 and φX174 phage were destroyed by radicals generated in the solution using the generating device, and DNA inside the cell were damaged. As a result, it was found that bacteria and viruses were led to be inactivated in the end.

Experiment 2 purpose of this Experiment 2 is to clarify the effect of indirect irradiation. In terms with the conditions, collecting 135 uL from PTW (MilliQ water irradiated by plasma) irradiated for a certain period of time, and mixing this with bacterial liquid (about $2\times10^8$/mL) 15 uL including *E. coli* ATCC13706, and preserving for 20 minutes at 20° C., and diluting gradually in a Petri dish of an agar medium. The number of the bacteria was measured 0, 1, 2, 4, 8, 16, 32 minutes after the irradiation. The result is shown (x) in FIG. 9.

Next, under the same conditions using φX174 phage instead of *E. coli*, the result is shown (x) in FIG. 10.

As shown in this figure, a high sterilization effect was observed not only in a direct irradiation, but also in a indirect irradiation. In other words, based on these experiments, the plasma activated ophthalmic solution, according to the embodiments, was found very effective for the inactivation of Adenovirus.

It is to be noted that the present invention is not limited to the above-described embodiments and modified examples, and various modifications are possible within the spirit and scope of the present invention. For example, the above-mentioned plasma activated solution can be applied not only to anti-Adenovirus agent for EKC, but also to other useful usages using other types of solution and container materials. Particularly, the radical activated solution can be used as a bactericide against bacteria and viruses on the surface of any organs or cells of the body parts. For example, the radical activated solution can be applicable for a bactericide for mouth bacteria by keeping the solution (PTW) in one's mouth.

Furthermore, it is noted that in order to achieve the above objects, it is also possible to embody the present invention as an generating method for a plasma activated ophthalmic solution that includes, as its steps, the characteristic units included in such a generating device, and as a program causing a computer to execute such steps. It should be also noted that such program can be distributed on a recording medium such as a CD-ROM and over a transmission medium such as the Internet.

What is claimed is:

1. A plasma activated ophthalmic solution generating device configured to generate a therapeutic ophthalmic solution for treating epidemic keratoconjunctivitis, the device comprising:
   a unit dose ophthalmic eyedrop container with a container body, the container body sealing a certain solution in a sterile state;
   a power supply unit;
   an insulating barrier arranged surrounding an insert space, the insert space comprising the unit dose ophthalmic eyedrop container inserted therein;
   a plasma generating electrode that is arranged on the insulating barrier, the insulating barrier creating a gap between the plasma generating electrode and the unit dose ophthalmic eyedrop container equal to a plasma irradiation distance ; and a high voltage generating unit connected to the power supply unit that is configured to be supplied with a power source from the power supply unit and apply high voltage electric current to the plasma generating electrode, wherein the plasma generating electrode, in response to the high voltage electric current from the high voltage generating unit being applied thereto, is configured to generate a plasma activated ophthalmic solution for curing epidemic keratoconjunctivitis by heating the certain solution.

2. The plasma activated ophthalmic solution generating device according to claim 1, wherein:

the high voltage generating unit is a low frequency (LF) band AC high voltage generating unit that applies AC voltage approximately 2-10 kV as a drive voltage and 30-80 KHz as a frequency, and the plasma generating electrode irradiates non-thermal equilibrium plasma onto the unit dose ophthalmic eyedrop container at atmospheric pressure by receiving high voltage electric current from the low frequency (LF) band AC high voltage generating unit.

3. The plasma activated ophthalmic solution generating device according to claim 2, wherein:

the certain solution in the unit dose ophthalmic eyedrop container is a plasma irradiating solution, approximately half a volume of the container body is filled with gas and air, and the high voltage generating unit further applies approximately 0.1-0.5 A as a drive current to the plasma generating electrode to generate the plasma activated ophthalmic solution.

4. The plasma activated ophthalmic solution generating device according to claim 3, wherein the plasma irradiating solution comprises super-pure water, sodium hyaluronate solution, or silver nitrate solution, or a mixed solution comprising any of the super-pure water, sodium hyaluronate solution, or silver nitrate solution.

5. The plasma activated ophthalmic solution generating device according to claim 1, wherein:

the plasma generation electrode comprises an electrode wire as a core and a dielectric coating a surface of the electrode wire, the plasma generating electrode is formed spirally, and the unit dose ophthalmic eyedrop container is mounted into a hollow space of the plasma generation electrode.

6. The plasma activated ophthalmic solution generating device according to claim 5 wherein- the plasma generating electrode comprises a dielectric, film, an inner surface of the dielectric and an outer surface of the dielectric are coated with a film-like electrode, the plasma generating electrode is rounded cylindrically, and the unit dose ophthalmic eyedrop container is inserted into the hollow space of the plasma generating electrode.

7. The plasma activated ophthalmic solution generating device according to claim 5, wherein:

a material of the electrode wire comprises any of flexible copper wire, stainless wire, aluminum wire, iron wire, or gold wire, or alloy wire comprising any of flexible copper wire, stainless wire, aluminum wire, iron wire, or gold wire, and a material of the dielectric is a polymer with a siloxane bond or a polymer having imide bonds of a plurality of aromatic compounds.

8. The plasma activated ophthalmic solution generating device according to claim 6, wherein:

a material of the electrode wire comprises any of flexible copper wire, stainless wire, aluminum wire, iron wire or gold wire, or alloy wire comprising any of flexible copper wire, stainless wire, aluminum wire, iron wire or gold wire, and a material of the dielectric is a polymer with a siloxane bond or a polymer having imide bonds of a plurality of aromatic compounds.

9. The plasma activated ophthalmic solution generating device according to claim 1, further comprising:

an insertion hole in which the unit dose ophthalmic eyedrop container is inserted;

a switch part that initiates plasma irradiation; and an indicator that indicates a completion of plasma irradiation to a user.

10. The unit dose ophthalmic eyedrop container operable to be inserted in the plasma activated ophthalmic solution generating device of claim 1, comprising a bottle cap connected to the container body.

11. The unit dose ophthalmic eyedrop container according to claim 10, wherein:

the certain solution in the unit dose ophthalmic eyedrop container is a plasma irradiating solution, wherein approximately half a volume of the container body is filled with gas and air, and wherein the unit dose ophthalmic eyedrop container is made up with low density polyethylene; and the plasma irradiating solution comprises super-pure water, sodium hyaluronate solution or silver nitrate solution, or a mixed solution comprising any of the super-pure water, sodium hyaluronate solution or silver nitrate solution.

12. The therapeutic ophthalmic solution for epidemic keratoconjunctivitis, wherein the therapeutic ophthalmic solution is generated by irradiating non-thermal equilibrium plasma onto a plasma irradiating solution at atmospheric pressure with the usage of the plasma activated ophthalmic solution generating device of claim 1.

13. The therapeutic ophthalmic solution for epidemic keratoconjunctivitis according to claim 12, wherein the plasma irradiating solution comprises super-pure water, sodium hyaluronate solution or silver nitrate solution, or a mixed solution comprising any of the super-pure water, sodium hyaluronate solution or silver nitrate solution.

14. A therapeutic method for epidemic keratoconjunctivitis, comprising:

(a) a setting step of setting the unit dose ophthalmic eyedrop container of claim 1 in a hollow space of the plasma activated ophthalmic solution generating device of claim 1 before an eyedrop instillation;

(b) an initiating step of initiating a switch of the plasma activated ophthalmic solution generating device as a trigger for starting plasma irradiation to the container;

(c) a taking out step of taking out the container from the plasma activated ophthalmic solution generating device after completing plasma irradiation; and (d) an eyedropping step of dropping the plasma activated ophthalmic solution onto an eye of a user within a predetermined period after removing a cap of the container.

15. The therapeutic method for epidemic keratoconjunctivitis according to claim 14, wherein the predetermined period is within 10 minutes from a completion of the plasma irradiation.

16. An eye-drop kit for curing epidemic keratoconjunctivitis, comprising: a package comprising the plasma activated ophthalmic solution generating device of claim 1 and the unit dose ophthalmic eyedrop container of claim 1.

17. A plasma activated ophthalmic solution generating device configured to generate a therapeutic ophthalmic solution for treating epidemic keratoconjunctivitis, the device comprising:
a unit dose ophthalmic eyedrop container with a container body sealing a solution in a sterile state;
a power supply unit;
an insulating barrier having an insert space, the insert space comprising the unit dose ophthalmic eyedrop container with the container body inserted therein;
a pair of plasma generating electrodes formed by a dielectric film that are arranged on opposing sides of the insulating barrier, the pair of plasma generating electrodes being parallel flat electrodes, a first one of the pair of plasma generating electrodes being a high-voltage electrode and a second one of the pair of plasma generating electrodes being a grounding electrode, the dielectric film comprises an electrode wire and a dielectric material coating a surface of the electrode wire; and
a high-voltage generating unit connected to the power supply unit that is configured to be supplied with a power source from the power supply unit and apply high-voltage electric that applies alternating current (AC) voltage approximately 2-10 kV as a drive voltage, 30-80 KHz as a frequency, and 0.1-0.5 A as a drive current,
wherein the pair of plasma generating electrodes, in response to high-voltage electric current from the high-voltage generating unit being applied thereto, are configured to generate a plasma activated ophthalmic solution for curing epidemic keratoconjunctivitis by heating the solution, and
wherein the insulating barrier creates a gap between the unit dose ophthalmic eyedrop container and the pair of plasma generating electrodes equivalent to a plasma irradiation distance.

18. The plasma activated ophthalmic solution generating device according to claim 17, wherein the insulating barrier comprises a gas sealed therein, the gas being at least one of air, helium, argon, nitrogen, and a combination thereof.

19. A method for generating a therapeutic ophthalmic solution for treating epidemic keratoconjunctivitis, comprising:
providing a plasma activated ophthalmic solution generating device, comprising: a unit dose ophthalmic eyedrop container with a container body sealing a solution in a sterile state; a power supply unit; an insulating barrier having an insert space, the insert space comprising the unit dose ophthalmic eyedrop container with the container body inserted therein; a pair of plasma generating electrodes formed by a dielectric film that are arranged on opposing sides of the insulating barrier, the pair of plasma generating electrodes being parallel flat electrodes, a first one of the pair of plasma generating electrodes being a high-voltage electrode and a second one of the pair of plasma generating electrodes being a grounding electrode, the dielectric film comprises an electrode wire and a dielectric material coating a surface of the electrode wire; and a high-voltage generating unit connected to the power supply unit that is configured to be supplied with a power source from the power supply unit and apply high-voltage electric that applies alternating current (AC) voltage approximately 2-10 kV as a drive voltage, 30-80 KHz as a frequency, and 0.1-0.5 A as a drive current, wherein the insulating barrier creates a gap between the unit dose ophthalmic eyedrop container and the pair of plasma generating electrodes equivalent to a plasma irradiation distance; and
applying high-voltage electric current from the high-voltage generating unit to the pair of plasma generating electrodes, thereby generating a plasma activated ophthalmic solution for curing epidemic keratoconjunctivitis through heating of the solution.

\* \* \* \* \*